United States Patent

Suite

Patent Number: 5,513,643
Date of Patent: May 7, 1996

[54] DISPOSABLE PROTECTION WRAP FOR USE WITH A SPHYGMOMANOMETER

[76] Inventor: Jean M. Suite, 169 Edenwald Ave., Mt. Vernon, N.Y. 10550

[21] Appl. No.: 233,859

[22] Filed: Apr. 26, 1994

[51] Int. Cl.$^6$ ..................................................... A61B 5/00
[52] U.S. Cl. ........................................... 128/686; 606/202
[58] Field of Search ...................... 128/686; 606/201–4; 604/307, 308

[56] References Cited

U.S. PATENT DOCUMENTS

| | | | |
|---|---|---|---|
| 2,758,593 | 8/1956 | Berman . | |
| 3,232,289 | 2/1966 | Zimmerman . | |
| 3,467,077 | 9/1969 | Cohen . | |
| 3,570,495 | 3/1971 | Wright . | |
| 3,606,880 | 8/1971 | Ogle, Jr. . | |
| 3,757,772 | 9/1973 | Goldblat . | |
| 3,765,405 | 10/1973 | Natkanski . | |
| 3,773,036 | 11/1973 | Weyer . | |
| 3,977,393 | 8/1976 | Kovacic . | |
| 4,176,664 | 12/1979 | Kalish | 604/307 |
| 4,192,299 | 3/1980 | Sabatano | 604/307 |
| 4,197,944 | 4/1980 | Catlin . | |
| 4,222,391 | 9/1980 | Rawson . | |
| 4,354,503 | 10/1982 | Golden . | |
| 4,548,249 | 10/1985 | Slaughterbeck . | |
| 4,967,758 | 11/1990 | Masciarotte . | |
| 5,201,758 | 4/1993 | Glover | 128/686 |
| 5,228,448 | 7/1993 | Byrd | 128/686 |
| 5,251,646 | 10/1993 | Bowen . | |

OTHER PUBLICATIONS

Product Brochure for "Disposa–Cuf" by Critikon, bearing copyright date of 1989.

*Primary Examiner*—Angela D. Sykes
*Assistant Examiner*—Robert L. Nasser, Jr.
*Attorney, Agent, or Firm*—Hopgood, Calimafde, Kalil & Judlowe

[57] ABSTRACT

A disposable non-porous protective wrap for use with a sphygmomanometer. When a person's blood pressure is taken, the protective wrap is applied to a limb of the person. Then, the sphygmomanometer cuff is applied over the protective wrap. The protective wrap insulates both the person and the sphygmomanometer from being exposed to diseases, germs and any other contaminants which may have been transferred onto the sphygmomanometer from other persons and does not interfere with the blood pressure reading.

5 Claims, 1 Drawing Sheet 5,513,643

DISPOSABLE PROTECTION WRAP FOR USE WITH A SPHYGMOMANOMETER

BACKGROUND OF THE INVENTION

This invention generally relates to equipment and methods used to take a person's blood pressure. In particular, it relates to the use of a protective wrap in conjunction with a sphygmomanometer.

Persons seeking medical care frequently have their blood pressure checked. This procedure is performed with a sphygmomanometer, which is used by wrapping an inflatable cuff around a person's limb (e.g., an arm or leg). The cuff is then inflated and deflated while a gauge on the sphygmomanometer is read to obtain the blood pressure. This procedure is repeated each time a medical treatment provider desires to take a person's blood pressure.

It is well known that persons seeking medical care can have varying types of skin diseases, rashes, ulcers, and/or abrasions. These conditions can occur on many areas of the body, including a person's upper and lower limbs. As a result of these conditions, the previously described procedure for using a sphygmomanometer can yield undesirable results when used in multiple patient settings, such as in a hospital or physician's office. In particular, if a sphygmomanometer is used on a person having contagious fluids exposed on the skin, the cuff on the sphygmomanometer may become contaminated with those fluids. Subsequent use of the same sphygmomanometer cuff on a second person will likely transfer the contaminated fluids to the second person and may subsequently cause infection.

Various devices that purportedly protect persons from contaminating each other due to the repeated use of a sphygmomanometer have been proposed. See, for example, U.S. Pat. Nos. 3,606,880; 3,757,722; 3,773,036; 4,548,249; 4,967,758 and 5,251,646. Each of the devices described in these patents, however, have one or more drawbacks which make their use impractical. For example, in U.S. Pat. Nos. 3,606,880; 3,757,722 and 3,773,036, the entire cuff is disposable so that the device is rather expensive to use. On the other hand, in U.S. Pat. Nos. 4,548,249; 4,967,758 and 5,251,646, various disposable protective liners or covers are placed around a sphygmomanometer cuff before each use, so that the protective covers are difficult and time consuming to use.

As a result, an inexpensive, easily used device is needed to prevent the spread of disease when using a sphygmomanometer.

SUMMARY OF THE INVENTION

In accordance with the present invention, a disposable protective wrap is provided for use with a sphygmomanometer when taking a person's blood pressure. The protective wrap is made of a section of non-porous, flexible material and has two ends. The wrap preferably has sufficient length to be wrapped around a limb of the person whose blood pressure is to be taken such that the two ends overlap. The wrap also preferably has a width greater than the width of the sphygmomanometer cuff. Fastening devices are provided on the wrap at each end so that the wrap can be secured around the person's limb prior to the application of the sphygmomanometer cuff to prevent direct contact between the cuff and the person's limb with no restriction of the cuff.

One object of the present invention is to provide a protective wrap that can be used in conjunction with a sphygmomanometer to eliminate the risk of contamination.

Another object of the present invention is to provide a protective wrap that has a simple design and is easily manufactured.

A further object of the present invention is to provide a protective wrap which allows blood pressure readings to be accurately and quickly taken.

Still another object of the present invention is to provide a protective wrap whose proper operation is independent of any blood pressure cuff.

DESCRIPTION OF THE PREFERRED EMBODIMENTS

Figure 1:
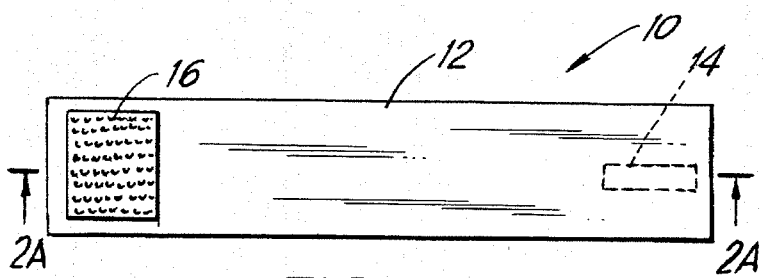
FIG. 1 is a plan view of a first embodiment of the protective wrap.
Figure 2:
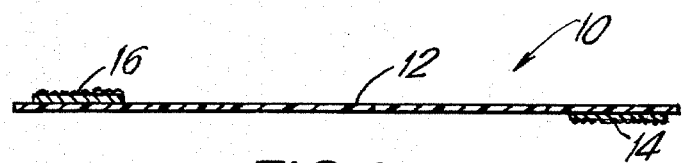
FIG. 2 is a cross-sectional view of FIG. 1 taken along line 2A—2A.

FIGS. 1 and 2 illustrate a first embodiment of the present invention wherein a protective wrap 10 is provided for use with a sphygmomanometer. The protective wrap 10 is manufactured from a section of flexible non-porous flexible material 12. Fastening devices 14 and 16 are also provided on the wrap 10.

In accordance with a preferred embodiment, the section of non-porous material 12 is substantially rectangular in shape. The material 12 preferably has sufficient length so that when wrapped around the limb of a person, the two ends of the material 12 on which the fastening devices 14 and 16 are attached overlap. The section of material 12 also preferably has a width which is greater than the width of the cuff of a sphygmomanometer. This configuration allows the protective wrap 10 to provide complete insulation between a person's limb and the sphygmomanometer cuff. As such, the protective wrap will prevent the transfer of any liquids or other contagions which are on a person's skin to the sphygmomanometer. It will also prevent the transfer of liquids or contagions from the sphygmomanometer to a person.

The non-porous material 12 from which the wrap 10 can be made is preferably a polyethylene material. Vinyl and rayon acetate materials, however, may also be utilized. Further, any non-porous material which has some flexibility so that it can be wrapped around a person's limb, can be used. In particular, however, the following materials (sold by Minnesota Mining and Manufacturing Company) may be utilized: 5.4 mil. (0.137 mm) polyethylene EVA (Product No. 9835); 7.0 mil. (0.178 mm) perforated polyethylene (Product No. 1766); 6.6 mil. (0.168 mm) perforated polyethylene EVA (Product No. 1527L/1527); 5.0 (0.127 mm) polyethylene printable (Product No. 1523); 2.8 mil. (0.071 mm) heatsealable film (Product No. 9958) and 8.0 mil. (0.203 mm) woven rayon acetate (Product No. 1538L/1538).

The fastening devices 14 and 16 are provided to allow the wrap 10 to be secured to a person's limb. The fastening devices 14 and 16 preferably comprise properly engaging hook and loop material such as VELCRO strips. Referring to FIGS. 1 and 2, the strips 14 and 16 are secured to opposite sides and opposite ends of the non-porous section of material 12. The strip 16 preferably has greater length than the strip 14 to allow the wrap 10 to be secured around various sized limbs. Although VELCRO strips are illustrated, any other fastening device can be used. By way of example only, properly aligned snaps can be used. As another example, a self-adhesive material can be used to construct the wrap 10 so that the ends of the wrap 10 stick to each other when wrapped around a person's limb. Various self-adhesing materials can be used to fasten the disposable wrap around a patient's limb. For example, the following materials (sold by Minnesota Mining and Manufacturing Co.) may be utilized: 9.0 mil (0.229 mm) Microporous Nylon Non-woven (Product No. 9903); 5.5 mil (0.140 mm) Microporous Rayon Non-woven (Product No. 1785); 11.5 mil (0.292 mm) Spun-Laced Polyester Non-woven (Product No. 1776) and 5.5 mil (0.140 mm) Microporous Rayon Non-woven with or without Liner (Product No. 1530L/1539).

Figure 5:
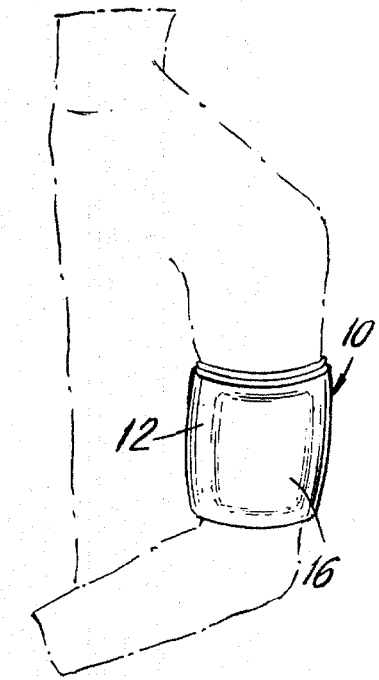
FIG. 5 shows the protective wrap of the present invention applied to an arm.

The protective wrap 10 of the present invention is preferably used in accordance with the following method. First, as illustrated in FIG. 5, the wrap 10 is placed around the arm of the person whose blood pressure is to be taken. The VELCRO strips 14 and 16 are engaged to secure the wrap 10 in place. Next, the sphygmomanometer cuff is placed around the person's arm and over the wrap 10 and then operated to determine the person's blood pressure. Once the blood pressure has been determined, the sphygmomanometer cuff is removed. The wrap 10 is then also removed and disposed of.

Figure 3:
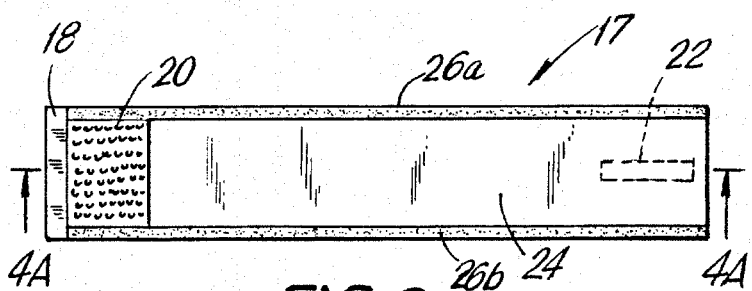
FIG. 3 is a plan view of a second embodiment of the protective wrap.
Figure 4:
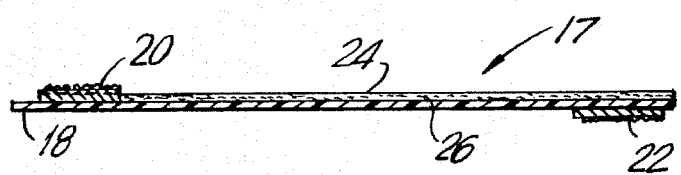
FIG. 4 is a cross-sectional view of FIG. 3 taken along line 4A—4A.

A second embodiment of the present invention is shown in FIGS. 3 and 4. A protective wrap 17 includes a flexible, non-porous material 18, fastening devices 20 and 22, and a liquid absorbent material 24 which lines the material 18. Reinforcing edges 26a and 26b are formed by folding the edges of the liquid absorbent material 24 over. These edges 26a and 26b form an elevated ridge which helps retain any liquid. When the wrap 17 is secured to a person's limb, prior to the application of the sphygmomanometer cuff, as illustrated in FIG. 5, the liquid absorbent material 24 makes direct contact with the person's skin and absorbs any fluid present on the person's skin. The absorbent material 24 thus serves to localize any liquid flow, such as bleeding or oozing of body liquids that may be occurring underneath the protective wrap 17, thereby assisting in preventing contamination of the sphygmomanometer cuff.

In accordance with another embodiment of the present invention, the liquid absorbing material 24 is also liquid dispensing. A sanitizing agent (e.g., betadine) is stored in the liquid dispensing material 24. When the wrap 17 is secured to the person's limb and the sphygmomanometer cuff is inflated, the agent is released onto the person's skin. In this case, absorbent material 24 then not only localizes the flow of contaminated liquids near the area of the sphygmomanometer cuff but also causes the area underneath the sphygmomanometer cuff with which the sanitizing agent comes into contact to be sanitized.

Various materials can be used as liquid absorbent and liquid dispensing materials. For example, a material sold by Johnson and Johnson called Nu-Gauze (Product No. H-22223372) can be used. Also, materials that are referred to as Curity Cleaners, manufactured and sold by the Kendall Co. of Boston, Mass. (Product Nos. 1429, 1913, 2057) can also be used in this invention.

While the present invention has been illustrated with specific embodiments, it is understood that various modifications to those embodiments will readily occur to persons with ordinary skill in the art. All such modifications and variations are deemed to be within the scope and spirit of the present invention as defined by the following claims to the invention.

What is claimed is:

1. A disposable protective wrap and sphygmomanometer system, comprising:

a section of non-porous, flexible material having two ends, where the section is adapted to be wrapped around a limb of a person so that the two ends overlap;

means for fastening one end of the section of material to the other end of the section when wrapped around the person's limb;

a sphygmomanometer having an inflatable cuff of a selected width adapted to be wrapped around the person's limb and over the section of non-porous, flexible material so that there is no direct contact between the sphygmomanometer cuff and the person's limb and no restriction of the cuff;

a liquid absorbent material layered to the section of non-porous, flexible material; and a sanitizing agent stored in the liquid absorbent material.

2. The system of claim 1 wherein the section of non-porous, flexible material has a width greater than the width of the sphygmomanometer cuff.

3. The system of claim 1 wherein the section of non-porous, flexible material has a substantially rectangular shape.

4. The system of claim 1 wherein the section of non-porous, flexible material is made from a polyethylene film.

5. The system of claim 1 wherein the fastening means include strips of hook and loop material attached to opposite ends and to opposite sides of the section of non-porous, flexible material.

* * * * *